United States Patent
Lim et al.

(10) Patent No.: US 7,260,434 B1
(45) Date of Patent: Aug. 21, 2007

(54) INTEGRATED 8-POLE FILTERED FEEDTHROUGH WITH BACKFILL TUBE FOR IMPLANTABLE MEDICAL DEVICES

(75) Inventors: Wisit Lim, Palmdale, CA (US); Rodney J. Hawkins, Saugus, CA (US); Kavous Sahabi, Winnetka, CA (US)

(73) Assignee: Pacesetter, Inc., Sylmar, CA (US)

( * ) Notice: Subject to any disclaimer, the term of this patent is extended or adjusted under 35 U.S.C. 154(b) by 105 days.

(21) Appl. No.: 10/949,073

(22) Filed: Sep. 23, 2004

(51) Int. Cl.
*A61N 1/372* (2006.01)
(52) U.S. Cl. ...................................... 607/37
(58) Field of Classification Search ............... 361/302; 607/36–37; 439/909
See application file for complete search history.

(56) References Cited

U.S. PATENT DOCUMENTS

| | | | |
|---|---|---|---|
| 5,620,476 A | 4/1997 | Truex et al. ............... 607/36 |
| 5,650,759 A | 7/1997 | Hittman et al. ........... 333/182 |
| 5,683,435 A | 11/1997 | Truex et al. ............... 607/37 |
| 5,751,539 A | 5/1998 | Stevenson et al. ......... 361/302 |
| 5,896,267 A | 4/1999 | Hittman et al. ........... 361/302 |
| 5,905,627 A | 5/1999 | Brendel et al. ............ 361/302 |
| 5,999,398 A | 12/1999 | Makl et al. ................ 361/302 |
| 6,349,025 B1 | 2/2002 | Fraley et al. .............. 361/302 |
| 6,414,835 B1 | 7/2002 | Wolf et al. ................ 361/302 |
| 6,424,234 B1 | 7/2002 | Stevenson ................. 333/182 |
| 6,519,133 B1 * | 2/2003 | Eck et al. .................. 361/302 |
| 6,529,103 B1 * | 3/2003 | Brendel et al. ............ 333/182 |
| 6,567,259 B2 * | 5/2003 | Stevenson et al. ......... 361/302 |
| 6,660,116 B2 | 12/2003 | Wolf et al. ............... 156/89.12 |
| 6,879,857 B2 * | 4/2005 | Swanson et al. ............. 607/36 |
| 2002/0027484 A1 * | 3/2002 | Stevenson et al. ......... 333/182 |
| 2002/0166618 A1 | 11/2002 | Wolf ....................... 156/89.12 |
| 2003/0040779 A1 * | 2/2003 | Engmark et al. ............ 607/36 |
| 2005/0119709 A1 | 6/2005 | Gauglitz et al. ............ 607/36 |

FOREIGN PATENT DOCUMENTS

| EP | 0870517 | 4/1997 |
| WO | WO99/67796 | 12/1999 |

* cited by examiner

*Primary Examiner*—Robert E. Pezzuto
*Assistant Examiner*—Jessica L. Reidel (57) ABSTRACT

A feedthrough apparatus for a implantable medical device having a casing includes a conductive housing having an outer side, an inner side, and a peripheral surface with a continuous assembly groove therein for mounting on the casing of the implantable medical device. The conductive housing has first and second through bores extending between the outer side and the inner side in spaced apart, generally parallel, relationship. First and second filtered feedthrough assemblies are received, respectively, in the first and second through bores. Each filtered feedthrough assembly includes an insulative terminal, a filter capacitor, and a plurality of lead wires electrically isolated from the conductive housing supported on and extending through the insulative terminal and through the filter capacitor in conductive relation therewith. Also, a backfill port is provided on the conductive housing and has a passageway extending between the inner side and the outer side.

19 Claims, 8 Drawing Sheets

INTEGRATED 8-POLE FILTERED FEEDTHROUGH WITH BACKFILL TUBE FOR IMPLANTABLE MEDICAL DEVICES

FIELD OF THE INVENTION

The present invention relates generally to implantable medical devices, such as cardiac pacemakers, cardioverters and defibrillators, and more particularly, to a feedthrough apparatus for connecting electronic circuits within an implantable medical device to the connector top and for providing electric field shielding and filtering.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, an ICD or implantable cardioverter-defibrillator for delivering electrical therapy to terminate ventricular tachycardia or ventricular fibrillation via an external connector assembly having lead-receiving receptacles. The appended claims are not intended to be limited, however, to any specific example or embodiment described herein.

ICDs and other implantable medical devices such as pacemakers are hermetically packaged to isolate the device from the body environment. Such devices require that electrical signals be passed between the packaged device and its external connectors, without compromising the hermeticity of the package. Depending on the configuration of the implantable device, there may be multiple electrical paths required between the device and its external connectors. These paths must be electrically and mechanically integrated with the device to provide a safe, long-term arrangement which does not compromise the hermetic package.

Typically, electrical coupling between the electronic circuits of the implantable device and the external connections provided by a connector assembly mounted outside of the implantable device are provided by a feedthrough assembly. The feedthrough assembly extends through the hermetically sealed outer wall of the device and into the connector assembly so as to couple the electronic circuits within the implantable device to lead-receiving receptacles within the connector assembly. Common feedthrough assemblies contain a number of wires equal to the number of electrical paths required for the configuration. The wires are placed in a ceramic sleeve and are sealed and mechanically secured to the sleeve, such as by brazing. The ceramic sleeve is secured to a weld ring, such as by brazing, following which the weld ring is integrated into the housing wall of the implantable device, such as by laser welding. The resulting feedthrough assembly has many individual seals and exposed lengths of wire.

Feedthrough assemblies of the type described have a number of potential problems. One such problem results from the large number of seals required. Because the plurality of wires and the weld ring each require a separate seal, the large number of seals increases the chances of a compromised seal and the resulting loss of hermeticity. Moreover, the exposed wires act as an antenna for environmental noise sources. Such noise compromises the quality of the signal transmitted, and this can lead to misinterpretation by the implantable device. Additionally, the wires can be damaged by misalignment or bending during handling of the feedthrough assembly.

Traditionally, single and dual chamber ICDs use a single feedthrough with the appropriate number of leads depending on the device's bore configuration.

Heart failure ICDs require eight leads due to the additional LV lead connector bore. This is accomplished by using two quad (four lead) filtered feedthrough assemblies. These parts consist of ceramic terminals, ceramic EMI capacitor, platinum-iridium wires and a titanium housing which encompasses the whole assembly. The titanium housing has a built-in flange for mounting and hermetically welding to the device.

The feedthrough wires are connected to the electronic assembly through solder joints to an output flex. The feedthroughs are located on the device case and laser welded in place during peripheral welding of the device.

The process of assembly and laser welding of two feedthroughs to the heart failure ICD devices have proven to be laborious and slow. Due to clearance needed between two feedthroughs to prevent reflection damage and weld interference, extra space is required for the device as well.

After peripheral welding, devices are backfilled with nitrogen. This is done through an opening called a backfill port which may be a separate titanium part welded onto the case. This requires a subassembly step with dedicated weld requirements and procedures. In addition careful positioning of the part is needed to make sure the port is not blocked off inside the device.

Typical disclosures of implantable medical devices having shielded and filtered feedthroughs can be found, for example, in U.S. Pat. Nos. 5,620,476 and 5,683,435 to Truex et al. comprising a feedthrough assembly in which plural wires are eliminated in favor of a single, monolithic structure of elongated configuration which extends through and is hermetically sealed to a sealing device such as a weld ring. The weld ring is, in turn, hermetically sealed within the housing wall of the implantable device. The monolithic structure comprises a multilayered structure in which an array of printed conductors provides the connections between the electronic circuits of the implantable device and the lead-receiving receptacles of the connector assembly. Electric field shielding of the printed conductors is provided by a conductive boot surrounding the printed conductors and being coupled to ground. The conductive boot may be provided by printed ground planes on opposite sides of the printed conductors within a multilayered structure. Filtering is provided by capacitors coupled between positive contacts and ground contacts within a second portion of the feedthrough assembly residing within the implantable device.

In another instance as presented in U.S. Pat. No. 6,349,025 to Fraley et al., a filtered feedthrough is disclosed that does not block passage of gas in a helium leak test and enables testing of the hermeticity of the feedthrough while inhibiting high voltage arcing in single filtered feedthrough and multiple filtered feedthrough array configurations. Still another instance is presented in U.S. Pat. No. 6,414,835 to Wolf et al. according to which a capacitive filtered feedthrough assembly is formed in a solid state manner to employ highly miniaturized conductive paths each filtered by a discoid capacitive filter embedded in a capacitive filter array. Yet another instance is presented in U.S. Pat. No. 6,660,116 to Wolf et al. which discloses a capacitive filtered feedthrough assembly formed in a solid state manner to employ highly miniaturized conductive paths each filtered by a discoid capacitive filter embedded in a capacitive filter array.

It was in light of the foregoing that the present invention was conceived and has now been reduced to practice.

SUMMARY

A feedthrough apparatus for an implantable medical device has a casing includes a conductive housing having an outer side, an inner side, and a peripheral surface with a continuous assembly groove therein for mounting on the casing of the implantable medical device. The conductive housing has first and second through bores extending between the outer side and the inner side in spaced apart, generally parallel, relationship. First and second filtered feedthrough assemblies are received, respectively, in the first and second through bores. Each filtered feedthrough assembly includes an insulative terminal, a filter capacitor, and a plurality of lead wires electrically isolated from the conductive housing supported on and extending through the insulative terminal and through the filter capacitor in conductive relation therewith. Also, a backfill port is provided on the conductive housing and has a passageway extending between the inner side and the outer side.

The invention comprises two ceramic terminals with each having four leads embodied in one titanium housing. The terminals are gold brazed in the housing as in the manner with current quad feedthroughs. EMI filter capacitors are attached to the terminals and housing in the same manner as performed with the current components.

In addition, the backfill port is designed as a feature of the housing. This construction saves additional assembly steps for that component. The backfill port is dimensionally configured to simulate the currently used backfill port and to minimize the functional impact to the current manufacturing process.

The integration of the backfill port to the housing is required but not limited to an eight pole feedthrough. It can easily be integrated into any other high voltage feedthrough to achieve similar manufacturing benefits.

The design of the Integrated eight pole feedthrough is based on achieving manufacturability improvements of feedthrough components, reducing thermal inputs to the feedthrough/output flex solder joints, enhancing weld requirements of feedthrough to case and reducing assembly processes. Once this feedthrough design is implemented, it will eliminate all manufacturing processes associated with locating and welding of the backfill port.

A primary feature, then, of the present invention is the provision of improved feedthrough apparatus for connecting electronic circuits within an implantable medical device to the connector top and for providing electric field shielding and filtering.

A further feature of the present invention is the provision of feedthrough apparatus which includes a conductive housing having an outer side, an inner side, and a peripheral surface with a continuous assembly groove therein for mounting on the casing of the implantable medical device, a pair of filtered feedthrough assemblies, each mounted on the conductive housing including an insulative terminal, a filter capacitor, and a plurality of lead wires electrically isolated from the conductive housing supported on and extending through the insulative terminal and through the filter capacitor in conductive relation therewith, and a backfill port on the conductive housing and having a passageway extending between the inner side and the outer side.

Another feature of the present invention is the provision of such feedthrough apparatus in a manner to improve peripheral welding efficiency and throughput by reducing complexity of weld path and simplifying the weld sequence with no wait time being required.

Yet another feature of the present invention is the provision of such feedthrough apparatus which reduces welding heat input to solder joints and rest of the assembly, thereby reducing scrap and resulting rejection rate.

Still a further feature of the present invention is the provision of such feedthrough apparatus which improves overall device assembly efficiency and lowers manufacturing cost by incorporating the back fill tube into the feedthrough housing thus removing two subassembly processes, namely, tack and peripheral weld of the backfill tube.

Still another feature of the present invention is the provision of such feedthrough apparatus which reduces component cost by utilizing fewer components.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
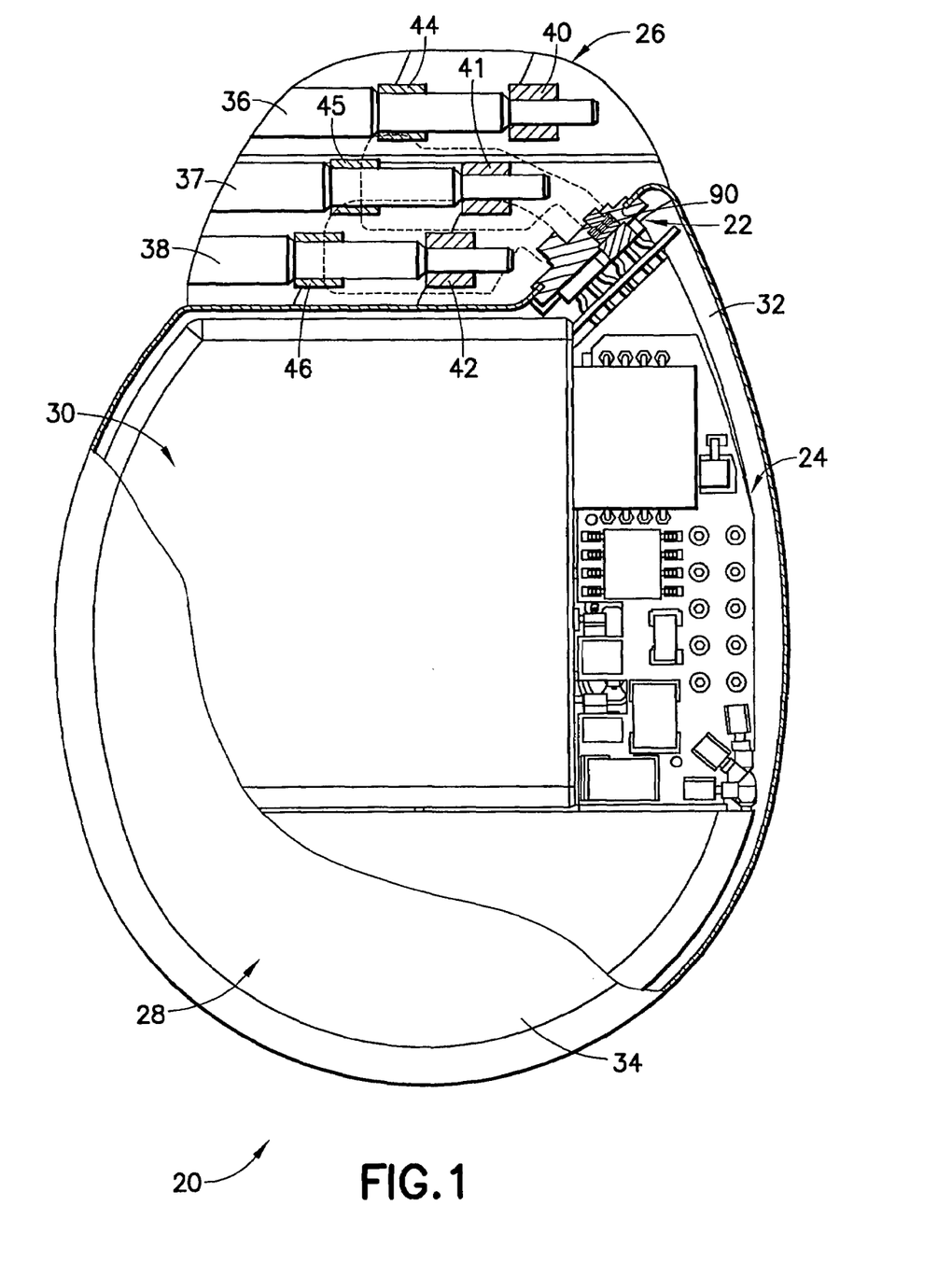
FIG. 1 is a side elevation view, partially cut away and in section, illustrating a medical implant device equipped with feedthrough apparatus embodying the present invention.
Figure 2:
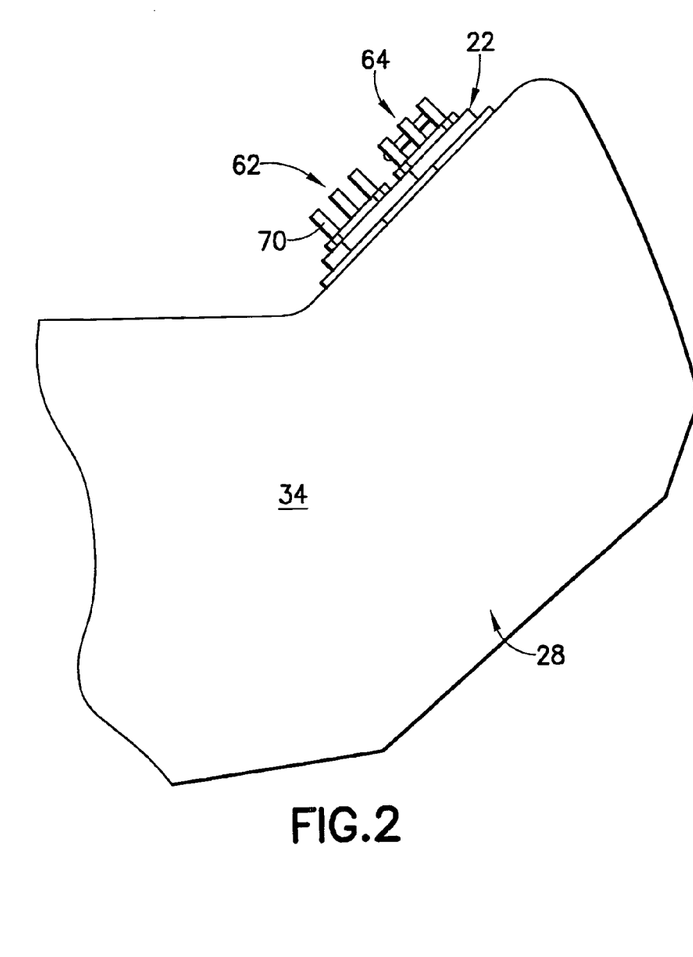
FIG. 2 is a detail side elevation view illustrating a portion of the medical implant device of FIG. 1.
Figure 3:
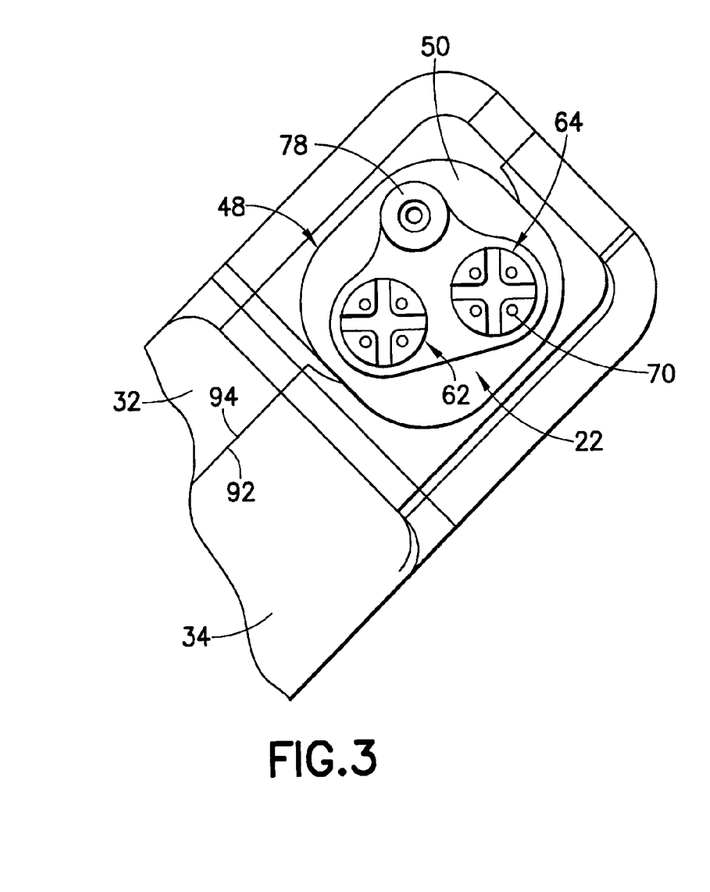
FIG. 3 is a plan view of one face of the medical implant device shown in FIG. 2.

Referring to FIG. 1, there is shown a perspective view of an implantable medical device 20 in the form of an ICD incorporating features of the present invention. Although the present invention will be described with reference to the embodiments shown in the drawings, it should be understood that the present invention can be embodied in many alternate forms or embodiments. In addition, any suitable size, shape or type of elements or materials compatible with the invention may be used.

The ICD 20 In FIG. 1 is seen to include feedthrough apparatus 22 in accordance with the present invention for electrically coupling electronic circuitry 24 of the device 20 to a connector assembly 26 mounted external to the hermetically sealed casing 28. The electronic circuitry 24 is powered by a battery 30, and both the electronic circuitry and the battery are contained within the hermetically sealed casing 28 comprised of opposed wall portions 32, 34. The connector assembly 26, which is mounted at the outside of the casing 28, includes a plurality of receptacles 36, 37, and 38 for receiving transvenous pacing leads in conventional fashion. Connector blocks 40, 41, and 42 are employed to make electrical connection, for example, to pin terminals of atrial and ventricular implantable leads (not shown), respectively. Connector blocks 44, 45, and 46 are employed to make electrical connection, for example, to ring terminals of atrial and ventricular implantable leads (not shown), respectively.

Turning now, in addition to FIG. 1, to FIGS. 2–9, the feedthrough apparatus 22 includes a conductive housing 48 having an outer side 50, an inner side 52 may be generally parallel with the outer side, and a peripheral surface 54 with a continuous assembly groove 56 therein for mounting on the casing 28 of the implantable medical device 20. The conductive housing 48 is preferably fabricated from titanium, but other metals such as niobium, tantalum, stainless steel, and alloys of those metals might also be employed, and has first and second through bores 58, 60 extending between the outer side 50 and the inner side 52 in spaced apart, generally parallel, relationship.

The feedthrough apparatus 22 also includes first and second filtered feedthrough assemblies 62, 64 received, respectively, in the first and second through bores 58, 60. The filtered feedthrough assemblies 62 and 64 are of identical construction and in the following description, the same reference numerals will be used for the components of each assembly. As seen particularly well in FIG. 9, each filtered feedthrough assembly 62, 64 includes an insulative terminal 66 preferably fabricated from a ceramic material such as alumina, zirconia, glass, and combinations of these materials, a filter capacitor 68, and a plurality of lead wires 70 composed of a conductive metal which may be, for example, niobium, platinum, platinum/iridium, titanium, tantalum, tungsten, molybdenum or alloys of those metals. The lead wires 70 which are electrically isolated from the conductive housing 48 are supported on both the insulative terminal 66 and on the filter capacitor 68 and extend from a first region residing within the connector assembly 26 and electronically coupled to respective connector blocks 40, 42 in the plurality of receptacles 36, 38 through the insulative terminal and through the filter capacitor and in conductive relation with the filter capacitor to a second region residing within the casing 28 and electrically coupled to the electronic circuitry 24 in the casing 28.

Conductive bonding material is introduced in each of the first and second through bores 58, 60 between the first and second filtered feedthrough assemblies 62, 64, respectively, and the conductive housing 48 for fixedly bonding the feedthrough assemblies to the conductive housing. Preferably, bonding of the insulative terminal 66 for each of the first and second filtered feedthrough assemblies 62, 64 is performed by the appropriate application of gold brazing material in a known fashion. Similarly, bonding of the filter capacitor for each of the filtered feedthrough assemblies 62, 64 is performed by the application of silver polyimide epoxy, also in a known fashion.

Figure 9:
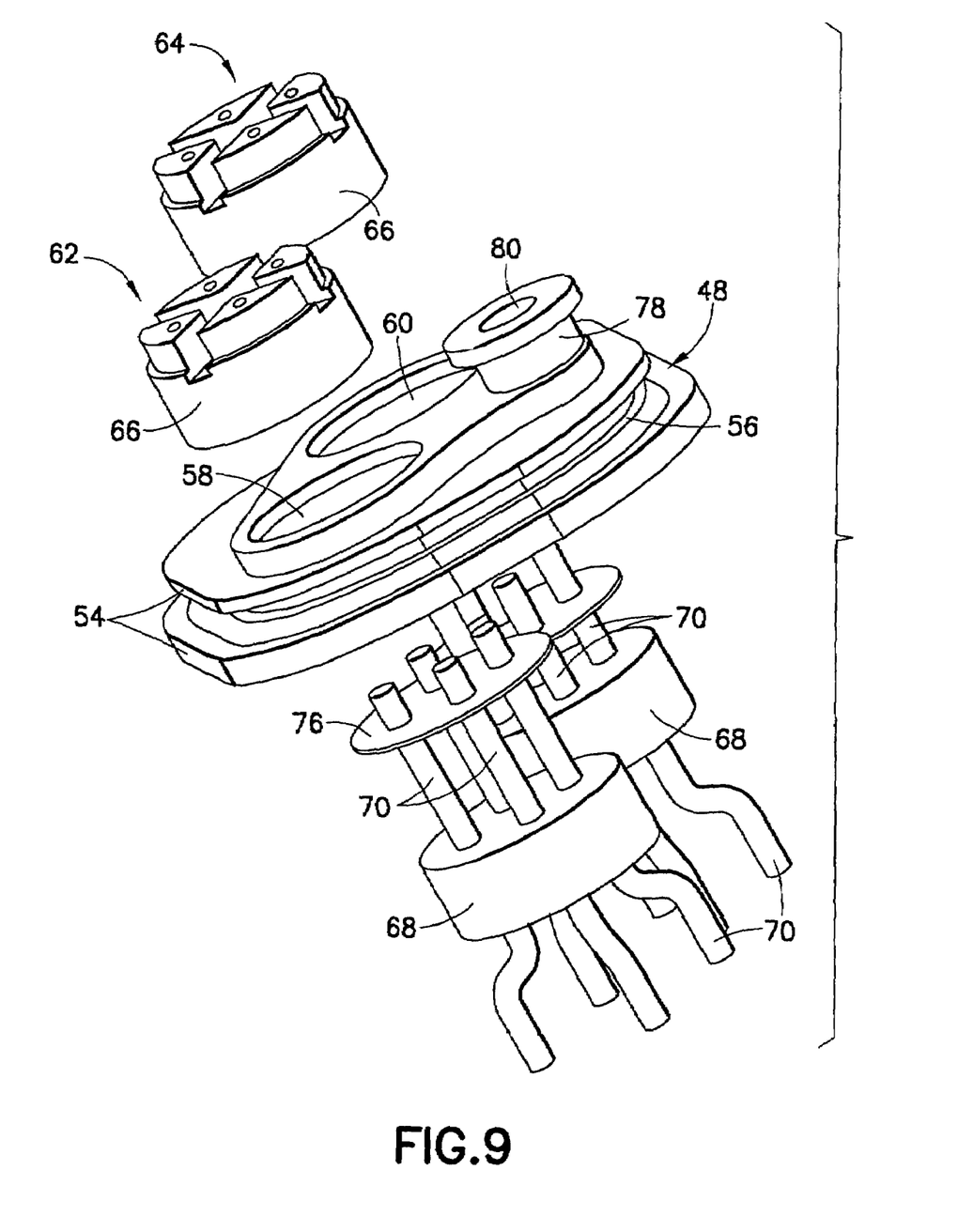
FIG. 9 is an exploded perspective view of the feedthrough apparatus of the invention.

As seen especially well in FIG. 9, a polyimide washer 76 is positioned intermediate the insulative terminal 66 and the filter capacitor 68 of each of the filtered feedthrough assemblies 62, 64 to isolate each of the lead wires 70 from one another.

Figure 8:
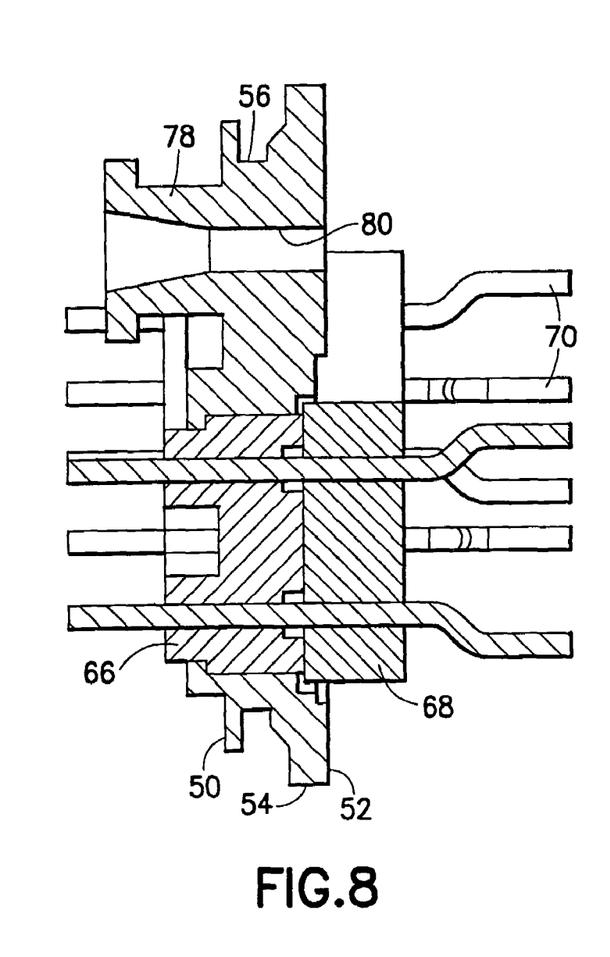
FIG. 8 is a cross section view taken generally along line 8—8 in FIG. 7.
Figure 8A:
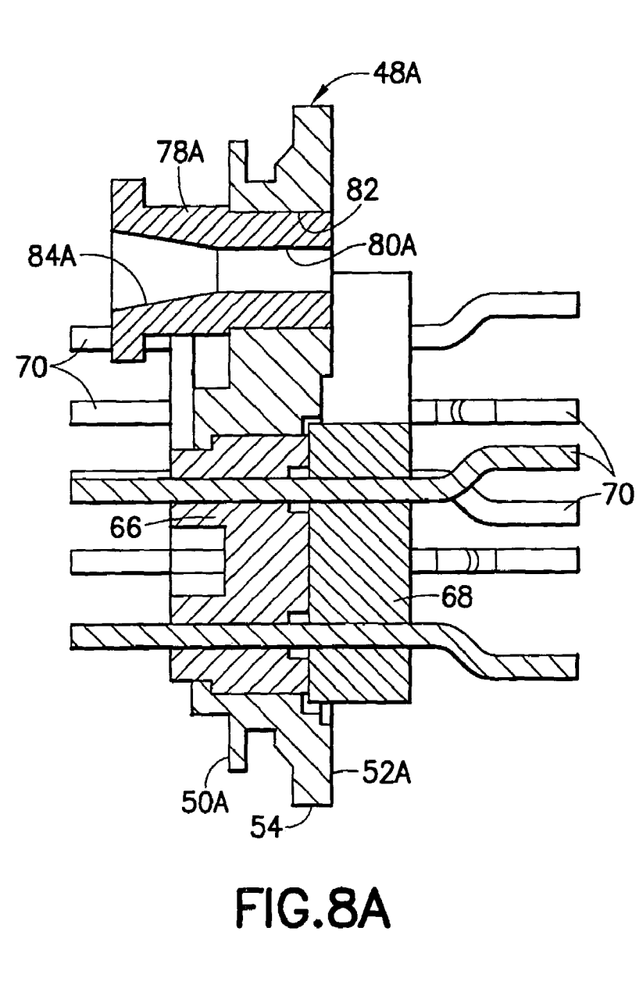
FIG. 8A is a cross section view illustrating a different embodiment of the invention.

As seen especially well in FIGS. 3–9, the feedthrough apparatus 22 also includes a backfill port 78 on the conductive housing 48 with a passageway 80 extending between the inner side 52 and the outer side 50. The backfill port 78 may be integral with the conductive housing 48 as illustrated in FIG. 8. In an alternative construction, as seen in FIG. 8A, a modified conductive housing 48A may have a third through bore 82 extending between an outer side 50A and an inner side 52A and generally parallel with the first and second through bores 58, 60. The backfill port 78A is a generally tubular member received in the third bore 82 and is sealingly fixed in any suitable manner to the conductive housing.

Figure 4:
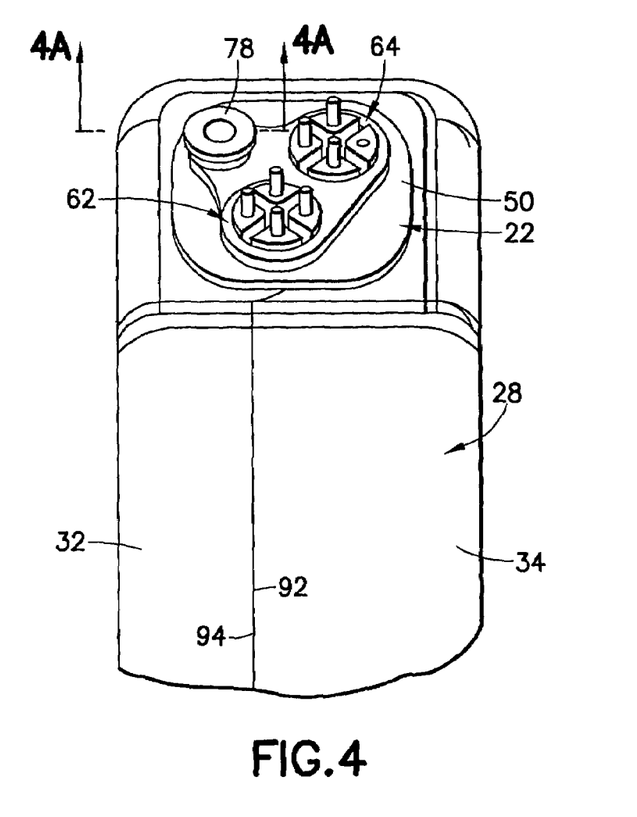
FIG. 4 is a detail end elevation view illustrating another portion of the medical implant device shown in FIG. 2.
Figure 4A:
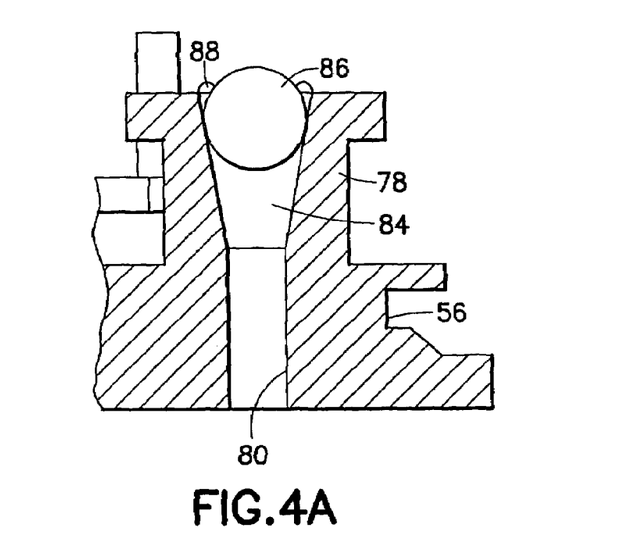
FIG. 4A is a cross section view taken generally along line 4A—4A in FIG. 4.
Figure 5:
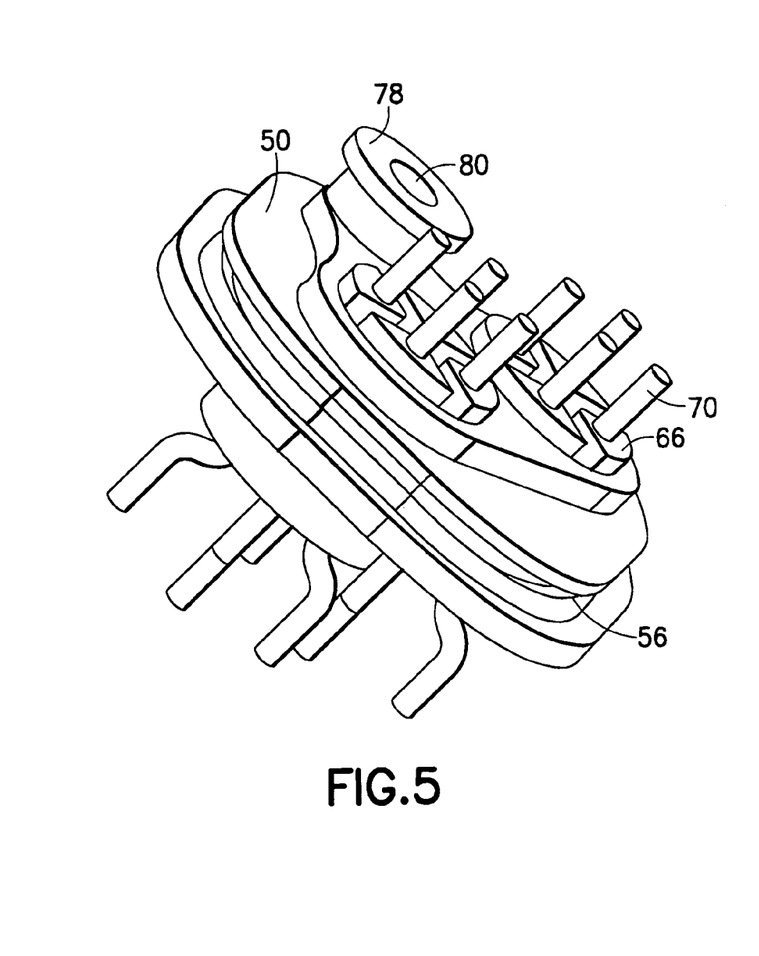
FIG. 5 is a perspective view of the feedthrough apparatus of the invention.
Figure 6:
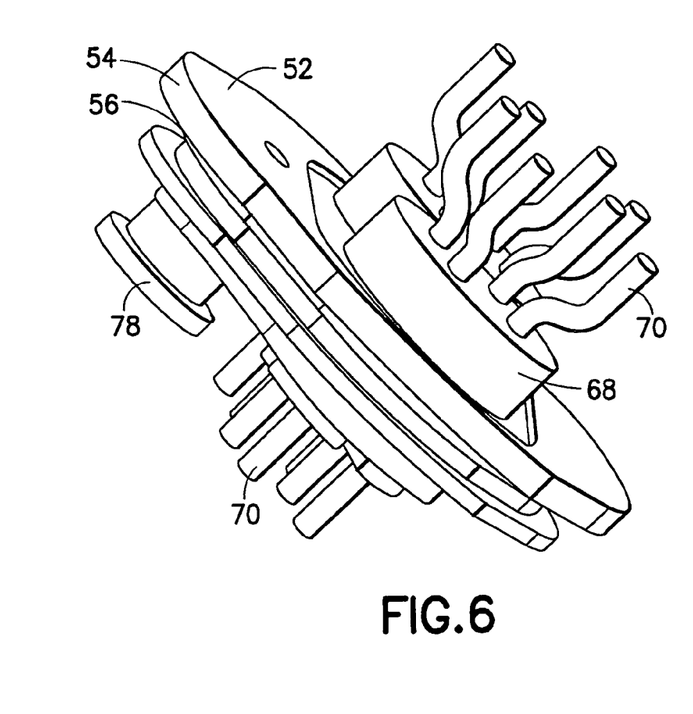
FIG. 6 is a perspective view of the feedthrough apparatus of the invention illustrated in FIG. 5, but from an opposite perspective.
Figure 7:
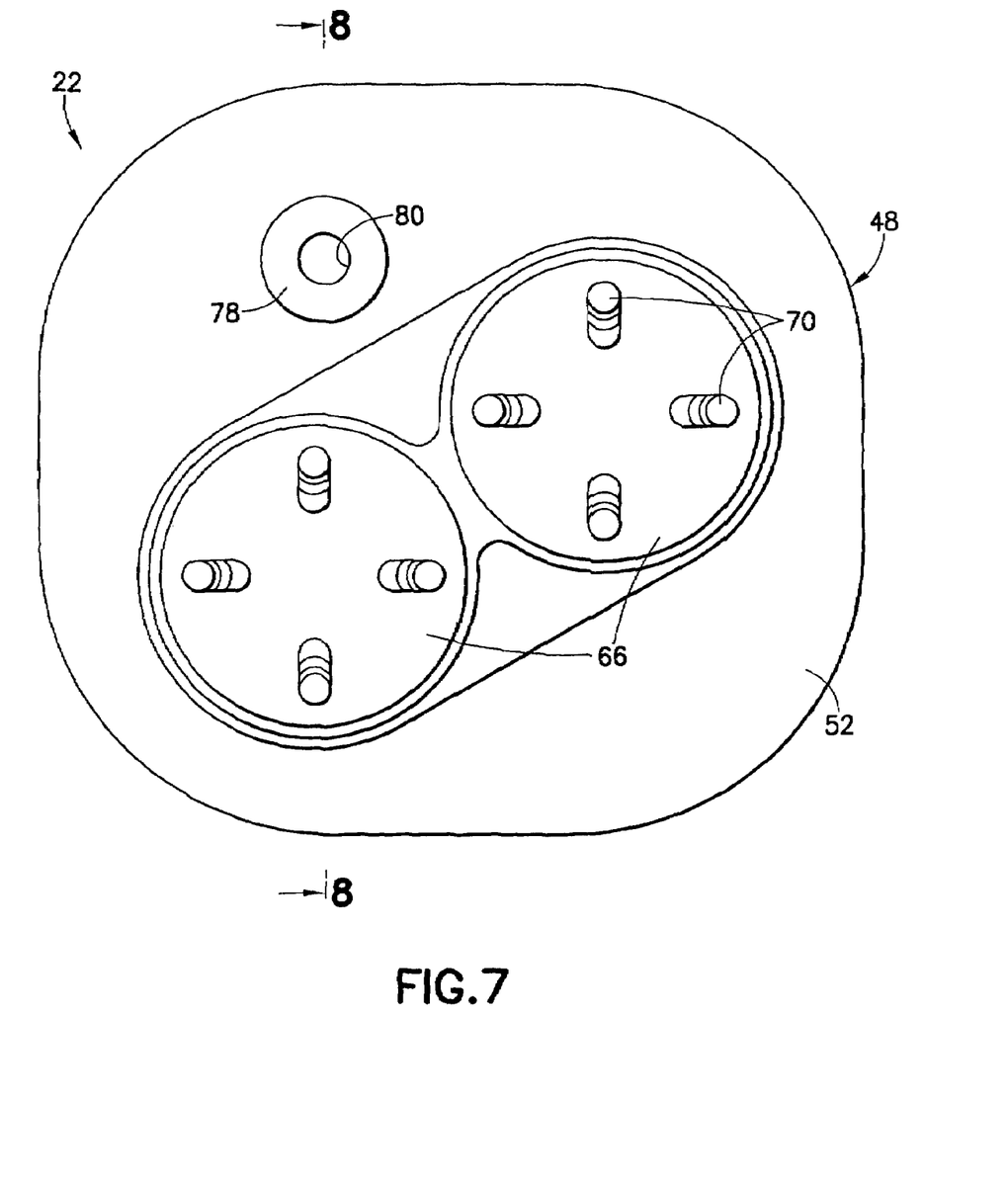
FIG. 7 is a bottom plan view of the feedthrough apparatus of the invention illustrated in FIGS. 5 and 6.

Turning back to FIG. 8 and especially to FIG. 4A which is an enlarged detail view of a portion of FIG. 8, it can be seen that the passageway 80 of the backfill port 78 has an outwardly facing orifice with a conical mouth 84 for fittingly receiving a metallic ball 86, preferably titanium, which is welded in place as indicated by weld line 88 for sealing the conductive housing after a backfill operation. The same provision exists for the modified conductive housing 48A with the modified backfill port 78A Having the construction as now described, the feedthrough apparatus 22 is united with the casing 28 of the implantable medical device 20. Specifically, the interface between the conductive housing 48 and the casing 28 is welded along the continuous assembly groove 56 for fixedly mounting the conductive housing to the casing of the implantable medical device. The identical procedure would be employed in the instance of the modified conductive housing 48A.

For the process of fabricating the implantable medical device 20 incorporating the feedthrough apparatus 22 of the invention, the conductive housing 48 is dimensioned to be received in an aperture 90 (FIG. 1) located in rims 92, 94 of the opposed wall portions 32, 34, respectively, of the casing 28 to be hermetically sealed. The conductive housing 48 is mounted in the aperture 90 of the first wall portion 32 of the conductive casing 28 such that the outer side 50 resides within the connector assembly 26, the inner side 52 resides within the eventually hermetically sealed casing, and the opposed wall portions 32, 34 of the casing are contiguously engaged with the assembly groove 56 of the conductive housing.

The proximal ends of the plurality of lead wires 70 on each of the filtered feedthrough assemblies 62, 64 are then bonded as by welding or soldering to the electronic circuitry 24 on the wall portion 32 and the distal ends of the plurality of lead wires 70 on each of the filtered feedthrough assemblies 62, 64 are then bonded as by welding to their associated connector blocks 40, 41, 42, 44, 45, 46 of the connector assembly 26. At this point in the process, the second wall portion 34 of the conductive casing 28 is attached to the first wall portion 32 so that their rims are contiguously positioned and so that the rim of the second wall portion 32 is contiguously engaged with the assembly groove 56 of the conductive housing 48. The rims 92, 94 of the wall portions 32, 34 of the casing 28 are then bonded as by welding to seal the interior of the casing from the exterior of the casing.

As a next step, the interface between the conductive housing 48 and the casing 28 of the implantable medical device 20 is welded along the continuous assembly groove 56 for fixedly mounting the conductive housing to the casing of the implantable medical device.

When the casing 28 has been fully integrated, all gases in the casing are removed by evacuating the casing. Nitrogen is then introduced into the casing in a suitable manner through the backfill port 78. The outlet of the backfill port 78, which is to say, the orifice or conical mouth 84 thereby hermetically sealing the casing of the implantable medical device. Immediately following this operation, the metallic ball 86, preferably titanium, is fittingly positioning in the conical mouth 84, then welded into place, for sealing the conductive housing 48.

Figure 10:
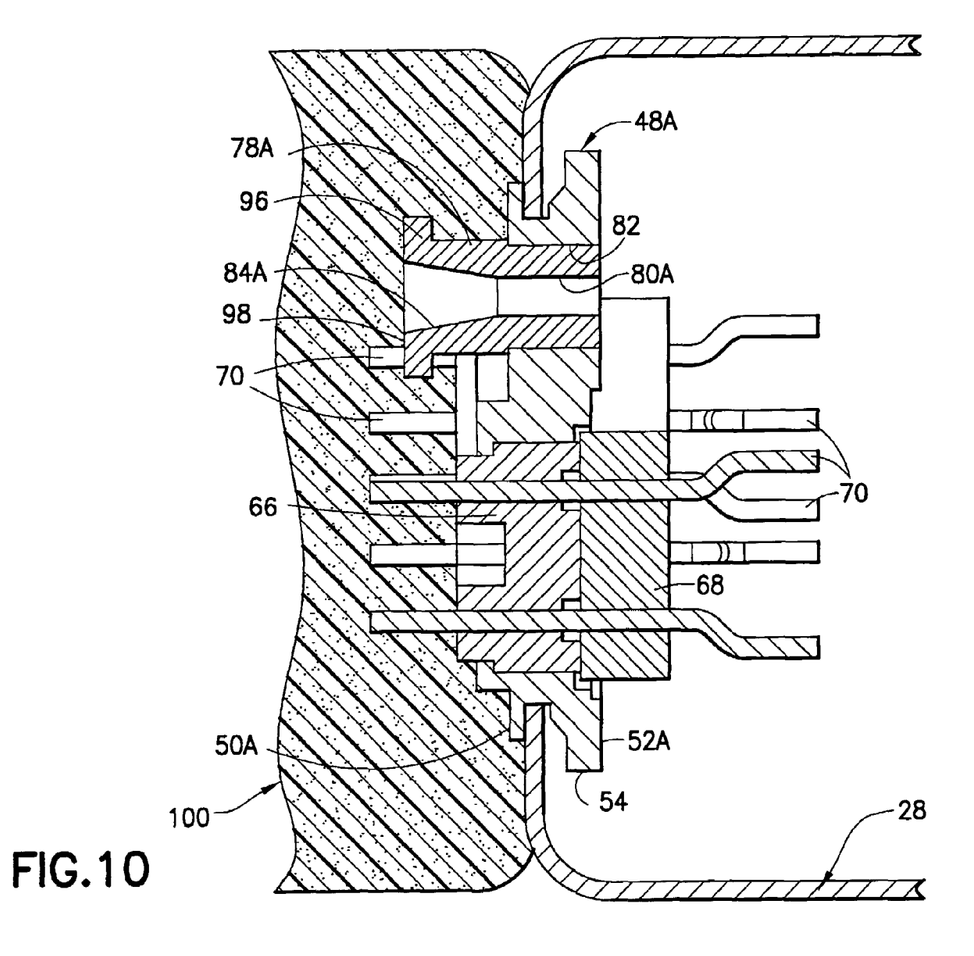
FIG. 10 is a cross section view, similar to FIGS. 8 and 8A illustrating still a different embodiment of the invention.

Consider now another feature of the invention which is best illustrated for purposes of description in FIG. 10. In this instance, the feedthrough apparatus shown similar to the FIG. 8A construction but which may be also be of the FIG. 8 construction, includes the backfill port 78A having an annular flange 96 surrounding the conical mouth 84A at an extreme end 98 of the backfill port. As here illustrated, a connector assembly 100 overlying the sealed casing is molded plastic of suitable composition. The annular flange 96 on the backfill port 78A is embedded in the molded plastic of the connector assembly 100 and thereby aids to hold the connector assembly in place on the casing 28.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A feedthrough apparatus for an implantable medical device having a casing and a connector assembly comprising:
   a conductive housing having an outer side, an inner side, and a peripheral surface with a continuous assembly groove therein for mounting on the casing of the implantable medical device;
   a first filtered feedthrough assembly mounted on the conductive housing comprising an insulative terminal, a filter capacitor, and a plurality of lead wires electrically isolated from the conductive housing supported on and extending through the insulative terminal and through the filter capacitor in conductive relation therewith;
   a second filtered feedthrough assembly mounted on the conductive housing comprising an insulative terminal, a filter capacitor, and a plurality of lead wires electrically isolated from the conductive housing supported on and extending through the insulative terminal and through the filter capacitor in conductive relation therewith, wherein the first and second filtered feedthrough assemblies are positioned in a side-by-side, spaced relationship; and
   a backfill port on the conductive housing and defining a passageway extending between the inner side and the outer side, the backfill port having a distal and proximal end, the proximal end located on the conductive housing, and the distal end having an annular flange, wherein the annular flange is embedded in the connector assembly of the implantable medical device.

2. The feedthrough apparatus as set forth in claim 1 wherein the conductive housing has first and second bores therethrough extending between the outer side and the inner side in spaced apart, generally parallel, relationship;
   wherein the first filtered feedthrough assembly is received in the first through bore; and
   wherein the second filtered feedthrough assembly is received in the second through bore.

3. The feedthrough apparatus as set forth in claim 2 wherein the backfill port is integral with the conductive housing.

4. The feedthrough apparatus as set forth in claim 3 wherein the passageway of the backfill port has an outwardly facing orifice with a conical mouth for fittingly receiving a metallic ball welded in place for sealing the conductive housing after a backfill operation.

5. The feedthrough apparatus as set forth in claim 4 wherein the annular flange surrounds the conical mouth.

6. The feedthrough apparatus as set forth in claim 4, wherein the metallic ball is composed of titanium.

7. The feedthrough apparatus as set forth in claim 2 wherein the conductive housing has a third bore therethrough extending between the outer side and the inner side; and
   wherein backfill port is a generally tubular member received in the third bore and sealingly fixed to the conductive housing.

8. The feedthrough apparatus as set forth in claim 7 wherein the third bore is generally parallel with the first and second bores.

9. The feedthrough apparatus as set forth in claim 7 wherein the passageway of the backfill port has an outwardly facing orifice with a conical mouth for fittingly receiving a metallic ball and welded in place for sealing the conductive housing after a backfill operation.

10. The feedthrough apparatus as set forth in claim 9 wherein the annular flange surrounds the conical mouth.

11. The feedthrough apparatus as set forth in claim 9, wherein the metallic ball is composed of titanium.

12. The feedthrough apparatus as set forth in claim 2 wherein the interface between the conductive housing and the casing of the implantable medical device is welded along the continuous assembly groove for fixedly mounting the conductive housing to the casing of the implantable medical device.

13. The feedthrough apparatus as set forth in claim 2 wherein conductive bonding material is introduced in the first bore between the first filtered feedthrough assembly and the conductive housing for fixedly bonding the first filtered feedthrough assembly to the conductive housing; and
   wherein conductive bonding material is introduced in the second bore between the second filtered feedthrough assembly and the conductive housing for fixedly bonding the second filtered feedthrough assembly to the conductive housing.

14. The feedthrough apparatus as set forth in claim 1
wherein the insulative terminal for each of the first and second filtered feedthrough assemblies is bonded to the conductive housing by the application of gold brazing material; and
wherein the filter capacitor for each of the first and second filtered feedthrough assemblies is bonded to the conductive housing by the application of silver polyimide epoxy.

15. The feedthrough apparatus as set forth in claim 1 including:
a polyimide washer intermediate the insulative terminal, and the filter capacitor of each of the first and second filtered feedthrough assemblies to isolate each of the lead wires from one another.

16. The feedthrough apparatus as set forth in claim 1
wherein the insulative terminal for each of the first and second filtered feedthrough assemblies comprises a ceramic material selected from the group consisting of alumina, zirconia, glass, and combinations thereof.

17. The feedthrough apparatus as set forth in claim 1
wherein the conductive housing comprises a metal selected from the group consisting of titanium, niobium, tantalum, stainless steel, and alloys thereof.

18. The feedthrough apparatus as set forth in claim 1
wherein each of the lead wires is composed of a metal selected from the group consisting of niobium, platinum, platinum/iridium, titanium, tantalum, tungsten, molybdenum and alloys thereof.

19. In an implantable medical device having an hermetically sealed casing including opposed wall portions enclosing electronic circuitry for producing electrical stimulating pulses and a battery for energizing the electronic circuitry and a connector assembly mounted on the sealed casing having a plurality of receptacles housing a plurality of connector blocks for engageably receiving one end of a medical electrical lead whose other end is in engagement with body tissue, feedthrough apparatus comprising:

a conductive housing comprising an outer side, an inner side, and a peripheral surface with a continuous assembly groove therein for mounting on the casing of the implantable medical device;

a first filtered feedthrough assembly mounted on the conductive housing comprising an insulative terminal, a filter capacitor, and a plurality of lead wires electrically isolated from the conductive housing supported on and extending from a first region residing within the connector assembly and electrically coupled to respective connector blocks in the plurality of receptacles through the insulative terminal and through the filter capacitor in conductive relation therewith to a second region residing within the casing and electrically coupled to the electronic circuitry in the casing;

a second filtered feedthrough assembly mounted on the conductive housing comprising an insulative terminal, a filter capacitor, and a plurality of lead wires electrically isolated from the conductive housing supported on and extending from a first region residing within the connector assembly and electronically coupled to respective connector blocks in the plurality of receptacles through the insulative terminal and through the filter capacitor in conductive relation therewith, the first and second filtered feedthrough assemblies positioned in side-by-side but spaced relationship to a second region residing within the casing and electronically coupled to the electronic circuitry in the casing; and a backfill port on the conductive housing and defining a passageway extending between the inner side and the outer side, the backfill port having a distal and proximal end, the proximal end located on the conductive housing, and the distal end having an annular flange, wherein the annular flange is embedded in the connector assembly of the implantable medical device.

\* \* \* \* \*